United States Patent
Hood et al.

(10) Patent No.: US 6,541,565 B2
(45) Date of Patent: Apr. 1, 2003

(54) POLYMERIC SYSTEM FOR DELIVERING AN ACTIVE MATERIAL

(75) Inventors: David K. Hood, Basking Ridge, NJ (US); Stephen L. Kopolow, Plainsboro, NJ (US); Michael Tallon, Aberdeen, NJ (US); Yoon Tae Kwak, Woodcliff Lake, NJ (US); Laurence Senak, West Orange, NJ (US); Drupesh Patel, Jersey City, NJ (US); John Mc Kittrick, Jersey City, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/882,415

(22) Filed: Jun. 15, 2001

(65) Prior Publication Data

US 2002/0058015 A1 May 16, 2002

Related U.S. Application Data

(63) Continuation-in-part of application No. 09/663,010, filed on Sep. 15, 2000, and a continuation-in-part of application No. 09/784,268, filed on Feb. 15, 2001.

(51) Int. Cl.$^7$ ................................................. C08K 3/00

(52) U.S. Cl. ...................................................... 524/808

(58) Field of Search ........................................ 524/808

(56) References Cited

U.S. PATENT DOCUMENTS

| | | | | |
|---|---|---|---|---|
| 5,130,121 A | * | 7/1992 | Kopolow et al. | 424/47 |
| 5,149,750 A | * | 9/1992 | Neissner et al. | 526/81 |
| 5,997,855 A | * | 12/1999 | Liu | 424/78.24 |

* cited by examiner

*Primary Examiner*—Edward J. Cain
(74) *Attorney, Agent, or Firm*—Walter Katz; William J. Davis; Marilyn J. Maue

(57) ABSTRACT

A system for delivering an active material includes (1) a stable, aqueous polymeric composition of (a) a water-soluble polymer having (b) in situ-formed, substantially water-insoluble resinous particles of said polymer substantially uniformly dispersed therein, and (c) water; and (2) an active material dispersed in said composition.

30 Claims, 1 Drawing Sheet

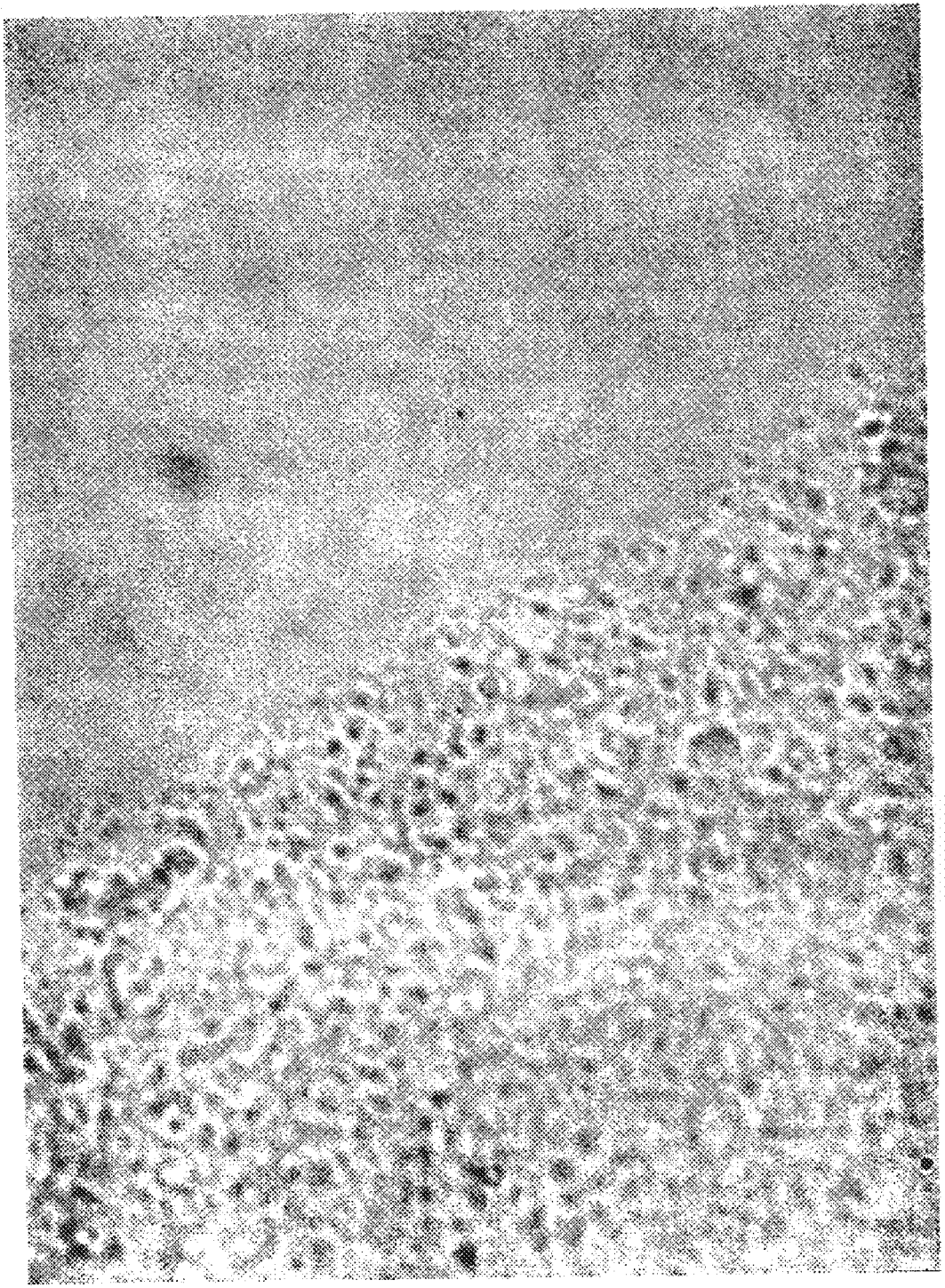

POLYMERIC SYSTEM FOR DELIVERING AN ACTIVE MATERIAL

CROSS-REFERENCE TO RELATED U.S. PATENT APPLICATIONS

This application is a continuation-in-part of co-pending U.S. patent application Ser. No. 09/663,010, filed Sep. 15, 2000 and 09/784,268, filed Feb. 15, 2001.

BACKGROUND OF THE INVENTION

1. Field of the Invention

This invention relates to polymeric delivery systems, and, more particularly, to a non-continuous, aqueous vinyl lactam polymeric composition having two phases therein, particularly suitable for delivering a water-insoluble active material dispersed therein.

2. Description of the Prior Art

Polymeric compositions of vinyl lactam monomers generally are one-phase, soluble, high viscosity materials. These compositions are found in a variety of commercial applications such as film formers, dye transfer inhibitors, rheology modifiers, dispersants, excipients, and drug delivery. Aqueous gels of these monomers can also be prepared by light covalent or associative crosslinking of polymer chains resulting in a highly swellable, one phase material of high viscosity. Such compositions are effective thickeners for use in personal care formulations such as hair care products.

The following prior art is representative of this technology.

Niessner, in U.S. Pat. Nos. 5,149,750 and 5,180,804, disclosed finely divided, water-swellable gel-like, water-swellable copolymers by polymerization of comonomers in the presence of a surfactant.

Liu, in U.S. Pat. No. 5,997,855, described a homogeneous terpolymer for hair care use, however, without a crosslinking agent.

Kopolow, in U.S. Pat. No. 5,130,121, described personal care compositions containing a stabilized cosmetically-active product obtained by in situ polymerization of a water-soluble vinyl monomer in the presence of discrete microdroplets of a cosmetically-active oil in water.

Blankenburg, in U.S. Pat. Nos. 5,635,169 and 6,107,397, described uncrosslinked aqueous copolymer dispersions of nonionic water-soluble monomers with N-vinyl groups, and hydrophobic monomers.

Steckler, in U.S. Pat. No. 3,878,175, disclosed highly absorbent spongy gel polymer materials by simultaneously copolymerizing and partially crosslinking a comonomer mixture of an alkyl acrylate and a heterocyclic N-vinyl monomer containing a carbonyl functionality in the presence of a hydrophobic liquid diluent in which the final polymer is insoluble.

Markus, in U.S. Pat. No. 2,810,716, described a process for making swellable resins by copolymerizing suitable monomers in the presence of a water-soluble non-redox divalent-ion containing salt.

Tseng, in U.S. Pat. Nos. 5,393,854 and 5,717,045, disclosed a one-phase, aqueous gel of crosslinked copolymers of vinyl pyrrolidone and dimethylaminoethyl methacrylate for use in hair care products. The crosslinking agent was 1-vinyl-3-(E)-ethylidene pyrrolidone. The gels had a Brookfield viscosity of between 60,000 and 100,000.

These references illustrate the desire of the art to produce a continuous network of polymer molecules, or microgel, which is a one-phase system, and of high viscosity.

Accordingly, it is an object of the present invention to provide a polymeric system capable of delivering an active material dispersed therein, which includes an aqueous polymeric composition which is not a gel but a combination of a film-forming polymer and substantially uniformly dispersed minute resinous particles, that, under suitable light magnification, shows the presence of two discrete phases therein, one phase including a water soluble polymer and the other phase constituting in situ-formed, water-insoluble resinous particles, and including an active material uniformly dispersed in said composition.

Another object of the invention is to provide an aqueous polymeric system for delivering active materials ordinarily present in personal care formulations, such as silicones, fragrances, sunscreens, and the like; in nutrient, medicament and pharmaceutical formulations, such as drugs, for example, aspirin, and syrups and the like.

These and other objects and features of the invention will be made apparent from the following description.

IN THE DRAWINGS

The FIGURE is a photomicrograph of the aqueous polymeric composition of the invention showing the presence of two discrete phases therein.

SUMMARY OF THE INVENTION

In accordance with a preferred embodiment of the present invention, there is provided a polymeric delivery system for an active material which includes (1) a stable, aqueous, two-phase polymeric composition which forms a clear to translucent film upon application to a substrate comprising, by weight, 5–75% of (a) a water-soluble polymer having (b) in situ-formed, substantially water-insoluble resinous particles of said polymer substantially uniformly dispersed therein, and (c) 25–95% of water; and (2) an active material suspended in the composition.

The active material for delivery from the polymeric system herein preferably is a hydrophobic, substantially water-insoluble material, which ordinarily is present in personal care formulations, such as silicones and fragrances, or an active material present in nutrient, medicament and pharmaceutical formulations, such as aspirin, syrups, and the like.

Preferably the polymer is a vinyl lactam polymer, optionally copolymerized with a methacrylate/acrylate and/or methacrylamide/acrylamide comonomer. Preferably the polymer is polyvinylpyrrolidone (PVP), poly(vinylcaprolactam) (PVCL), a copolymer of PVP and/or PVCL, and, optionally, one or more comonomers, including comonomers such as dimethylaminopropyl(meth)acrylamide (DMAPMA) and dimethylaminoethyl(meth)acrylate (DMAEMA).

In this invention the composition includes particles having a size of <500µ, preferably <100µ, and optimally between >1 nm and <500µ.

Suitably, the composition includes a substantially water-insoluble polymer which is a crosslinked or branched polymer, neutralized and/or quaternized, and/or functionalized quaternized. The ratio of (a):(b) is 20–95% to 5–80%, preferably 20–75% to 25–80%. The crosslinking agent suitably is a substantially water-insoluble compound, preferably pentaerythritol triallyl ether (PETE), or pentaerythritol tetraacrylate (PETA), preferably at least partially soluble in water. The crosslinking agent suitably is present in an amount of 0.02–0.5% by weight of said composition, preferably 0.05–0.3%.

In this invention, the two-phase composition has a Brookfield viscosity of 1,000 to 45,000 cps, preferably 2,000 to 20,000.

As a feature of the invention, there is provided herein a process for making a stable, aqueous polymeric composition which includes the steps of providing a reaction mixture of a water-soluble vinyl monomer, optionally with one or more water-soluble comonomers, a predetermined amount of a crosslinking agent and water, heating the mixture, then periodically adding a predetermined amount of an initiator, such as an azo initiator, and polymerizing at about 30–130° C., optionally further including the step of diluting with water during or after the polymerization.

The compositions herein may be dried if desired to provide the polymeric composition as a solid, and, if desired, the water soluble polymer can be extracted with a solvent. The dried, stable polymeric composition thereby includes, by weight, (a) 20% to 95% of a water-soluble polymer, and (b) 5% to 80% of in situ-formed, substantially water-insoluble resinous particles of said polymer substantially uniformly dispersed therein.

DETAILED DESCRIPTION OF THE INVENTION

The aqueous polymeric composition, having two phases therein, which are (a) a water-soluble polymeric phase and (b) a discrete, water-insoluble polymer particle phase, is generated in-situ during the polymerization of the monomers. In the preferred forms of the invention, the polymerization is carried out in aqueous solution of a vinyl lactam monomer, such as vinyl pyrrolidone or vinyl caprolactam. Optionally a comonomer may be present to form a copolymer. Suitable comonomers include methacrylate/acrylate monomers, such as dimethylaminoethyl(meth)acrylate (DMAEMA) and/or methacrylamide/acrylamide monomers, such as dimethylaminopropylacrylamide (DMAPMA).

This stable, aqueous polymeric composition forms a clear to translucent film upon application to a substrate and comprises, by weight, 5–75% of (a) a water-soluble polymer having (b) in situ-formed, substantially water-insoluble resinous particles of said polymer substantially uniformly dispersed therein, and (c) 25–95% of water.

The active material for delivery herein usually are those actives ordinarily found in personal care products such as skin and hair care products, or drugs which are administered in a sustained or time release mode. Both water-insoluble and water-soluble actives can be used. Generally the active material is dispersed in the polymeric composition by neutralization or chelation.

The invention will now be illustrated in more detail by reference to the following examples.

EXAMPLE 1

Two-Phase Polymeric Composition of VP/DMAPMA

1. To a 2-l kettle fitted with a nitrogen inlet tube, thermocouple, agitator, and feed lines was added 87.15 g of vinyl pyrrolidone monomer, (VP), 697 g DI water and 0.275 g (0.25% based upon monomer) of pentaerythritol triallyl ether (PETE) as crosslinker.
2. Purged with nitrogen subsurface for 30 minutes.
3. Heated to 70° C.
4. In a separate container weighed out 22.69 g of dimethylaminopropyl methacrylamide (DMAPMA).
5. With kettle temperature at 70° C., stop subsurface nitrogen purge and purged above surface. Precharged 1.1 g DMAPMA from container.
6. Started continuous addition of the remaining DMAPMA (21.86 g) over 210 minutes at a flow rate 0.11 ml/minute. Once the DMAPMA flow started, initiated with first shot of Vazo® 67 in isopropanol (IPA) (Time 0).
7. Initiator was added in 5 separate shots at 0, 30, 60, 150 and 210 minutes. 0.2 g of Vazo® 67 in 1.0 g IPA was added for each shot and two 0.5 g IPA washes were made.
8. Held the reaction temperature overnight at 70° C.
9. When residual VP level was below 400 ppm, diluted the batch with 266.7 g of DI water.
10. Cooled batch to 50° C.
11. Neutralized the batch with conc. HCl to pH of 6.2–6.8 at 50° C. Room temperature pH was 6.8–7.2. Required approximately 14 g of conc. HCl.
12. Added 0.15 to 0.19% BTC 50 NF as preservative.
13. A two-phase, aqueous polymeric composition as shown in the FIGURE was obtained.

EXAMPLE 2

The process of Example 1 was repeated using 5 separate shots of 0.3 g each of Vazo® 67 in 1.0 g of IPA. A similar polymeric composition as in Example 1 was obtained.

EXAMPLE 3

The process of Example 1 was repeated using 5 separate shots of 0.4 g each of Vazo® 67 in 1 g of IPA, and 0.3 g of crosslinker. A similar polymeric composition was obtained.

EXAMPLE 4

Polymeric Composition of PVP

1. To a 2-l kettle fitted with a nitrogen inlet tube, thermocouple, agitator, and feed lines was added 131.81 g of VP, 756 g DI water and 0.197 g PETE (0.15% based upon monomer).
2. Purged with nitrogen subsurface for 30 minutes.
3. Heated to 70° C.
4. Initiator was added at 0 and 30 minutes. 0.48 g of Vazo® 67 in 1.5 g IPA was added for each shot and two 1.0 g IPA washes were made.
5. Held the reaction temperature overnight at 70° C.
6. When residual VP was below 400 ppm, diluted the batch with 320.04 g DI water.
7. Cooled batch to 50° C.
8. Added 0.15 to 0.19% BTC 50 NF as preservative.
9. The product was a 2-phase, polymerization composition with 40 to 70% resinous particles, whose soluble fraction had a weight average molecular weight of 1,200,000 to 1,500,000.

EXAMPLE 5

VP/DMAPMA Neutralized with Benzophenone-4

1. To a 2-l kettle fitted with a nitrogen inlet tube, thermocouple, agitator, and feed lines was added 87.15 g of HPVP, 630 g DI water and 0.33 g PETE (0.30% based upon monomer).
2. Purged with nitrogen subsurface for 30 minutes.
3. Heated to 70° C.
4. Weighed out 22.69 g DMAPMA and 67 g DI water. Purged with nitrogen.
5. When kettle temperature was at 70° C., stopped subsurface nitrogen purge and purged above surface. Precharged 4.23 g DMAPMA/water from container.

6. Started a continuous addition of the remaining DMAPMA/water (85.46 g) over 210 minutes. Flow rate 0.40 ml/minute. Once DMAPMA/water flow started, initiated with first shot of Vazo® 67 in IPA (Time 0).
7. Initiator was added at 0, 30, 60, 150 and 210 minutes. 0.4 g of Vazo 67 in 1.0 g IPA was added for each shot and two 0.5 g IPA washes were made.
8. Held the reaction temperature overnight at 70° C.
9. When residual VP was below 400 ppm, diluted the batch with 266.7 g DI water.
10. Cooled batch to 50° C.
11. Neutralized the batch with benzophenone-4, 5 to 99 mole % (2 to 38.6 g respectively). Continued neutralization with sulfuric acid to pH of 6.8 to 7.8 at 50° C.
12. Cooled and discharged.
13. Product.

EXAMPLE 6

VP/DMAPMA

1. To a 2-l kettle fitted with a nitrogen inlet tube, thermocouple, agitator, and feed lines was added 104.58 g of HPVP, 756 g DI water and 0.59 g pentaerythritol tetraacrylate (0.30% based upon monomer).
2. Purged with nitrogen subsurface for 30 minutes.
3. Heated to 70° C.
4. In a separate container, weighed out 27.23 g DMAPMA and 80.4 g DI water. Purged with nitrogen.
5. When kettle temperature was at 70° C., stopped subsurface nitrogen purge and purged above surface. Precharged 5.38 g DMAPMA/water from container.
6. Started continuous addition of the remaining DMAPMA/water (102.25 g) over 210 minutes. Flow rate 0.52 ml/minute. Once DMAPMA/water flow started, initiated with first shot of Vazo® 67 in IPA (Time 0).
7. Initiator was added at 0, 30, 60, 150 and 210 minutes. 0.16 g of Vazo® 67 in 1.0 g IPA was added for each shot and two 0.5 g IPA washes were made.
8. Held the reaction temperature overnight at 70° C.
9. When VP was below 400 ppm, diluted the batch with 266.7 g DI water.
10. Cooled batch to 50° C.
11. Neutralized the batch with conc. sulfuric acid to pH of 6.6 to 7.8 at 25° C.
12. Added 0.15 to 0.19% BTC 50 NF as preservative.
13. Product.

EXAMPLE 7

Vinyl Caprolactam/DMAPMA Composition

1. To a 2-l kettle fitted with a nitrogen inlet tube, thermocouple, agitator and feed lines was added 130.7 g vinyl caprolactam, 128.7 g DI water, 171.6 g ethanol, and 0.88 g PETE (0.6% based upon monomer).
2. Purged with nitrogen for 30 minutes.
3. Heated to 70° C.
4. In a syringe pump was added 32.98 g DMAPMA and 171.6 g DI water.
5. At 70° C. added 40 ml of the DMAPMA/water mixture to the kettle and added the first shot of initiator, 0.075 g Vazo® 67 in 0.75 g ethanol. Washed with 0.75 g ethanol.
6. Started addition of the remaining DMAPMA/water mixture (Time 0) from the syringe pump at a rate of 0.34 ml/min, added over 480 minutes.
7. At time 60, 120, 180, 240, 300, 360, 420 and 480 minutes added a shot of Vazo® 67, 0.075 g in 0.75 g ethanol. Washed with 0.75 g ethanol.
8. Held at 70° C. overnight.
9. Cooled reaction to 30° C. and added 415.6 g DI water.
10. Mixed until uniform and then added 544.4 g DI water and 15.38 g hydrochloric acid.
11. Mixed for 2 hours. Adjusted pH to 6.6 to 7.8 with hydrochloric acid, if necessary.
12. Added 0.15 to 0.19% BTC-50 NF as preservative.
13. Product.

EXAMPLE 8

VP/DMAEMA Composition

1. To a 2-l kettle fitted with a nitrogen inlet tube, thermocouple, agitator, and feed lines is added 87.15 g of HPVP, 630 g DI water and 0.33 g (0.30% based upon monomer) pentaerythritol triallyl ether.
2. Purged with nitrogen subsurface for 30 minutes.
3. Heated to 70° C.
4. In a separate container, weighed out 22.69 g DMAEMA and 67 g DI water. Purged with nitrogen.
5. When kettle temperature was at 70° C., stopped subsurface nitrogen purge and purged above surface. Precharged 4.23 g DMAEMA/water from container.
6. Started continuous addition of the remaining DMAEMA/water (85.46 g) over 210 minutes. Flow rate 0.40 ml/minute. Once DMAEMA/water flow started initiator addition with first shot of Vazo 67 in IPA (Time 0).
7. Initiator was added at 0, 30, 60, 150, and 210 minutes. 0.4 g of Vazo 67 in 1.0 g IPA was added for each shot and two 0.5 g IPA washes were made.
8. Held the reaction temperature overnight at 70° C.
9. When VP was below 400 ppm, diluted the batch with 266.7 g DI water.
10. Cooled batch to 50° C.
11. Neutralized the batch with conc. HCl to pH of 6.2 to 6.8 at 50° C. Room temperature pH will be 6.8 to 7.2. Required approximately 14 g of conc. HCl.
12. Added 0.15 to 0.19% BTC 50 NF as preservative.

EXAMPLE 9

Drying of Example 8

The solution of Example 8 was dried on a drum dryer to a solids content of >95%. The Tg of the powder was 167° C.

EXAMPLE 10

Particle Isolation and Properties 95.2 g of approximately 10% solids content of the two-phase polyvinylpyrrolidone composition of Example 4 was diluted in 2-liters of distilled water and stirred until thoroughly mixed. A second solution was prepared by taking 500 ml of the first solution and diluting in 2-liters of distilled water. Stirred until thoroughly mixed. Poured the second solution into four 16 oz. jars and centrifuged at ~2250 rpm for about 90 minutes. A white precipitate was observed on the bottom of each 16 oz. jar. The precipitate was removed via pipette and placed into four 8-dram vials, respectively. The four 8-dram vials were centrifuged at ~3000 rpm for 60 minutes. The particle size of the precipitate was measured using a Microtrak UPA and found to be about 4 nm.

EXAMPLE 10A

The precipitate obtained in Example 10 in three 8-dram vials was dried, in vacuo, in a 40° C. oven overnight. The result was a thin, generally clear film upon visual observation. This material was then exposed successively to methanol, diethyl ether and n-heptane. After 24 hours, methanol had redispersed the material. Diethyl ether and n-heptane did not appear to effect the dried material. After 14 days, all samples exhibited a similar appearance to the original 24 hour observations. The particle size on the methanol dispersed material was measured using a Microtrak UPA and found to be about 4 microns.

COMPARATIVE EXAMPLE 11

An aqueous solution of 119.64 g of vinyl pyrrolidone monomer, 0.36 g pentaerythritol triallyl ether (PETE), 0.6 g of Vazo 67, and 480 g water was charged to a kettle and purged with nitrogen. The reaction mixture was then heated to 65° C. while stirring at 650 rpm. Within 25 minutes the product became so viscous that the reaction was stopped. The product was a continuous gel only.

COMPARATIVE EXAMPLE 12

An aqueous solution of 119.64 g of vinyl pyrrolidone monomer, 0.36 g pentaerythritol triallyl ether (PETE), 0.23 g of Vazo 67, and 480 g water was charged to a kettle and purged with nitrogen. The reaction mixture was then heated to 65° C. while stirring at 650 rpm. After 2 hours at 65° C., the reaction was heated to 95° C. for 1 hour. The product was a viscous solution only.

EXAMPLE 13

100 g of VP/DMAPA/PETE $H_2SO_4$, (10% solids) was mixed with 0.01 g of a red food dye and 2 g D-limonene (fragrance) to give a homogeneous dispersion. Addition of 0.5 g of Xama-7 (aziridine) crosslinker crosslinked the mixture. A hydrogel formed in 2 hours at RT without further mixing. The product was a homogeneous dispersion, red gel with an orange odor, similar to an air-freshener.

Similarly modified hydrogels can be formed with other commercial hydrogel systems such as contact lens membranes and hydrogel delivery systems.

EXAMPLE 14

| UV Coating Formulation | |
|---|---|
| Ingredient | Parts by Weight |
| VP/DMAPMA/PETE/BENZO-4 (Ex. 6) | 2.00 |
| PV-OH (88% hydrolyzed) | 8.00 |
| Sequrez ® 755 (glyoxyl) | 0.75 |
| Water | 89.25 |
| | 100.00 |

EXAMPLE 15

| Sunscreen Cream | |
|---|---|
| Ingredients | Wt. % |
| PHASE A | |
| Deionized water | 15.69 |
| Disodium EDTA | 0.10 |

| -continued | |
|---|---|
| Sunscreen Cream | |
| Ingredients | Wt. % |
| Acrylates/Steareth-20 Methacrylate Copolymer | 1.00 |
| Acrylates Copolymer | 1.00 |
| Hexylene Glycol | 1.00 |
| Glyceryl Polymethacrylate and Propylene Glycol and PVM/MA Copolymer | 0.50 |
| VP/DMAPMA/PETE/Benzophenone-4 Copolymer (Ex. 5) | 50.00 |
| PHASE B | |
| Glyceryl Stearate and Behenyl Alcohol and Palmitic and Stearic Acid and Lecithin and Lauryl and Myristyl Alcohol and Cetyl Alcohol | 5.00 |
| Oxybenzone | 3.00 |
| Octyl Salicylate | 3.00 |
| Tridecyl Neopentanoate | 2.00 |
| Octyl Palmitate | 6.00 |
| Myristyl Myristate | 1.00 |
| PHASE C | |
| Deionized Water | 5.00 |
| NaOH, 10% Solution | 1.26 |
| PHASE D | |
| Diazolidinyl Urea and Iodopropynyl Butylcarbamate | 0.50 |
| Methyl Paraben | 0.20 |
| Hexylene Glycol | 1.00 |
| PHASE E | |
| Fragrance | 0.25 |

Procedure
1. Combine ingredients in Phase A and heat to 70–75° C.
2. Combine ingredients in Phase B and mix and heat to 70–75° C.
3. Add Phase B to Phase A under homogenization.
4. Add Phase C to the batch under homogenization and homogenize for 15 minutes.
5. Switch to propeller mixing and cool to 45° C.
6. Add Phase D at 45° C. Add Phase E at 40° C. QS with water.

The UV absorbance of the cream was enhanced by the presence of the polymeric composition of the invention therein, as compared to similar formulations without this composition, generally an increase of about 2–3 SPF numbers.

EXAMPLE 16

| Pharmaceutical Tablet Composition | |
|---|---|
| Acetaminophen | 93.5% |
| PVP/PETE (in place of Polyplasdone K-90) (Ex. 4) | 4% |
| Polyplasdone XL | 2% |
| Magnesium Stearate | 0.5% |
| Total | 100% |

EXAMPLE 17

Perfume 0.25 g of D-limonene was mixed 0.25 g of the two-phase composition of poly(VP/DMAPMA/PETE)-HCl salt, and 2 ml $H_2O$ water added, and mixed vigorously with a magnetic stirrer for 30 minutes. Then added 97.5 g of water was added, and mixed for 2 minutes. The emulsion was then centrifuged for 20 minutes at 3000 rpm to remove any free D-limonene. Free D-limonene was decanted off and the dispersed limonene-containing composition was a clear translucent solution. A sample of 0.25% D-limonene in water alone was also centrifuged and decanted as a control. D-limonene is an orange smelling fragrance which is insoluble in water. Indeed, the poly(VP/DMAPMA/PETE) containing formulation had a pungent orange smelling fragrance which was significantly stronger than the control. Furthermore, it demonstrates that nano-particle technology can be manipulated for perfumes, fragrance extenders like air-fresheners, as well as many other time released/smart delivery systems. GC analysis will confirm the level of D-limonene present.

EXAMPLE 18

Silicone Oil Delivery

A mixture of 0.5 g silicone 200 oil and 0.5 g poly(VP/DMAPMA/PETE)-HCl salt, (100% solids) was vigorously agitated by magnetic stirrer for 30 minutes. The polymer particles swelled in the oil as the oil entered the polymer composition. Then 5 ml of water was added and the mixture was stirred for an additional hour. A thick, white emulsion was obtained. Added 98.5 g of water to obtain a 0.5% silicone encapsulate with 0.5% polymer in water. Centrifuged the mixture for 2 hours at 3000 rpm and decanted to remove the non-encapsulated material, i.e. free silicone oil. The product was then analyzed by FT-IR for the presence of silicone, using a ZnSe disk, and drying to form a film. The solutions were optically clear. The IR profile for the product vs. silicone oil itself showed the presence of encapsulated silicone oil in the polymer composition and no free silicone.

EXAMPLE 19

Pharmaceutical Active Delivery System

Naproxen free acid, whose optical activity is $[\alpha]_D^{25}=+66°$, 1.02 g was added to 40.77 g of VP/DMAPMA/PETE (10.9% solids, pH=10.1). The final pH was 8.0. The final solution exhibited translucent properties.

EXAMPLE 20

Pharmaceutical Active Dispersion

Dried VP/DMAPMA/PETE/sulfuric acid 0.40 g was added to 0.05 g of Naproxen free acid. 14.85 g of ethanol was added to this mixture and then agitated for 2 hours. The solution was dried in a 60° C. vacuum oven, in vacuo. 14.5 g of water was added to the dried mixture. Visually, the sample appeared uniformly dispersed. After 10 days some solid settling was observed, but the solution still appeared cloudy.

While the invention has been described with particular reference to certain embodiments thereof, it will be understood that changes and modifications may be made which are within the skill of the art.

Accordingly, it is intended to be bound only by the following claims, in which:

1. A system for delivering an active material comprising (1) a stable, aqueous polymeric composition comprising, (a) a water soluble polymer having (b) in situ-formed, substantially water-insoluble resinous particles of said polymer substantially uniformly dispersed therein, and (c) water; and (2) an active material suspended in said composition.

2. A composition according to claim 1 wherein said active material is a personal care, nutrient, or a pharmaceutically active material.

3. A composition according to claim 1 wherein said polymer is polyvinylpyrrolidone (PVP) or poly (vinylcaprolactam) (PVCL).

4. A composition according to claim 1 wherein (1) comprises, by weight, 5–75% of (a) and (b), and 25–95% of (c).

5. A composition according to claim 1 wherein said polymer is a copolymer of PVP or PVCL and one or more comonomers.

6. A composition according to claim 5 wherein said comonomer is dimethylaminopropyl(meth)acrylamide (DMAPMA) and dimethylaminoethyl(meth)acrylate (DMAEMA).

7. A composition according to claim 1 wherein said polymer is a copolymer of PVP and PVCL and one or more comonomers.

8. A composition according to claim 1 wherein said particles are <500µ.

9. A composition according to claim 8 wherein said particles are <100µ.

10. A composition according to claim 8 wherein said particles are >1 nm and <500µ.

11. A composition according to claim 1 wherein said substantially water-insoluble polymer is a crosslinked or branched polymer.

12. A composition according to claim 1 wherein said polymer is neutralized and/or functionally neutralized and/or quaternized, and/or functionalized quaternized.

13. A composition according to claim 1 wherein the ratio of (a):(b) is 20–95% to 5–80%.

14. A composition according to claim 13 wherein said ratio is 20–75% to 25–80%.

15. A composition according to claim 11 wherein said crosslinking agent is a substantially water-insoluble compound.

16. A composition according to claim 15 wherein said crosslinking agent is pentaerythritol triallyl ether (PETE), or pentaerythritol tetraacrylate (PETA).

17. A composition according to claim 12 wherein said functional neutralization acid is a UV active based upon derivatives of cinnamic and/or benzoic and/or sulfonic and/or acetic and/or terephthalic and/or maleic acids.

18. A composition according to claim 12 wherein said functional neutralization acid is a pharmaceutically active acid.

19. A composition according to claim 12 wherein said functional neutralization acid is optically active.

20. A composition according to claim 12 wherein said functional neutralization acid contains silicone.

21. A composition according to claim 12 wherein said functional neutralization acid modifies the refractive index of the polymer film composition.

22. A composition according to claim 16 wherein said crosslinking agent is present in an amount of 0.02–0.5% by weight of said composition.

23. A composition of claim 22 wherein said amount is 0.05–0.3%.

24. A composition according to claim 1 having a Brookfield viscosity of 1,000 to 45,000 cps.

25. A composition of claim 24 wherein said viscosity is 2,000 to 20,000.

26. A composition of claim 1 wherein said polymer is a vinyl lactam polymer, optionally copolymerized with a methacrylate/acrylate and/or methacrylamide/acrylamide comonomer.

27. A composition according to claim 1 which is dried to provide the polymeric composition as a solid.

28. A composition according to claim 27 which is dried and the water soluble polymer extracted with a solvent.

29. A dry, stable polymeric composition for delivering an active material comprising, by weight, (a) 20% to 95% of a water-soluble polymer, (b) 5% to 80% of in situ-formed, substantially water-insoluble resinous particles of said polymer substantially uniformly dispersed therein, and (c) a substantially water-insoluble active material suspended in said composition.

30. A dry, stable polymeric composition according to claim 29 wherein both (a) and (b) are polyvinylpyrrolidone (PVP).

\* \* \* \* \*